United States Patent
Jadhav et al.

(10) Patent No.: US 12,428,733 B2
(45) Date of Patent: *Sep. 30, 2025

(54) PASSIVATION COMPOSITION BASED ON MIXTURES OF PHOSPHORIC AND PHOSPHONIC ACIDS

(71) Applicant: Henkel AG & Co. KGaA, Duesseldorf (DE)

(72) Inventors: Aditi Jadhav, Chinchwad (IN); Girdhari Kumar, Troy, MI (US); Meenu Vijay, Pune (IN)

(73) Assignee: Henkel AG & Co. KGaA, Duesseldorf (DE)

( * ) Notice: Subject to any disclaimer, the term of this patent is extended or adjusted under 35 U.S.C. 154(b) by 887 days.

This patent is subject to a terminal disclaimer.

(21) Appl. No.: 17/244,152

(22) Filed: Apr. 29, 2021

(65) Prior Publication Data
US 2021/0254219 A1  Aug. 19, 2021

Related U.S. Application Data

(63) Continuation of application No. PCT/EP2019/080949, filed on Nov. 12, 2019.

(51) Int. Cl.
| | |
|---|---|
| C23C 22/07 | (2006.01) |
| C07C 59/01 | (2006.01) |
| C23C 22/17 | (2006.01) |
| C23C 22/36 | (2006.01) |
| C23C 22/42 | (2006.01) |
| C23C 22/83 | (2006.01) |
| C23C 22/00 | (2006.01) |
| C23C 22/34 | (2006.01) |

(52) U.S. Cl.
CPC ........... *C23C 22/361* (2013.01); *C07C 59/01* (2013.01); *C23C 22/368* (2013.01); *C23C 22/42* (2013.01); *C23C 22/83* (2013.01)

(58) Field of Classification Search
CPC .............................................. C23C 22/06–23
See application file for complete search history.

(56) References Cited

U.S. PATENT DOCUMENTS

| | | |
|---|---|---|
| 2,559,878 A | 7/1951 | Johnson |
| 3,063,877 A | 11/1962 | Schiffman |
| 3,501,352 A | 3/1970 | Shah |
| 3,647,569 A | 3/1972 | Schneider |
| 3,932,198 A | 1/1976 | Schneider |
| 4,171,231 A | 10/1979 | Bishop et al. |
| 4,263,059 A | 4/1981 | Guhde et al. |
| 4,349,392 A | 9/1982 | Huvar |
| 4,359,345 A | 11/1982 | Da Fonte, Jr. |
| 4,359,346 A | 11/1982 | Da Fonte, Jr. |
| 4,359,347 A | 11/1982 | Da Fonte, Jr. |
| 4,359,348 A | 11/1982 | Crotty |
| 4,367,099 A | 1/1983 | Lash et al. |
| 4,384,902 A | 5/1983 | Crotty et al. |
| 4,578,122 A | 3/1986 | Crotty |
| 5,743,971 A | 4/1998 | Inoue |
| 5,855,695 A | 1/1999 | McMillen et al. |
| 6,203,854 B1 | 3/2001 | Affinito |
| 2003/0188807 A1 | 10/2003 | Meagher |
| 2011/0008645 A1* | 1/2011 | Schneider ............ C23C 22/364 |
| | | 106/287.18 |
| 2011/0162556 A1 | 7/2011 | Banda et al. |
| 2014/0360630 A1 | 12/2014 | Arnold et al. |
| 2017/0009363 A1 | 1/2017 | Hiramatsu et al. |
| 2017/0314137 A1 | 11/2017 | Schneider et al. |

FOREIGN PATENT DOCUMENTS

| | | |
|---|---|---|
| CN | 102011112 A | 4/2011 |
| CN | 102046842 A | 5/2011 |
| CN | 102471890 A | 5/2012 |
| CN | 102639750 A | 8/2012 |
| DE | 3213384 A1 | 12/1982 |
| DE | 19733972 A1 | 2/1999 |
| DE | 102007021364 A1 | 11/2008 |
| DE | 102010001686 A1 | 8/2011 |
| EP | 2014793 A2 | 1/2009 |
| EP | 2695970 A1 | 2/2014 |
| GB | 1461244 A | 1/1977 |

(Continued)

OTHER PUBLICATIONS

International Search Report for International Application PCT/EP2019/080949 mailed Jan. 14, 2020.
International Search Report for PCT/EP2019/061344, mailed Jul. 3, 2019.

*Primary Examiner* — Lois L Zheng

(74) *Attorney, Agent, or Firm* — Mary K. Cameron

(57) ABSTRACT

The present invention provides an aqueous passivation composition for the treatment of zinc or zinc alloy coatings, comprising:

i) phosphoric acid;

ii) at least one water-soluble polyphosphonic acid or a water-soluble salt thereof, iii) at least one divalent metal cation ($M^{2+}$); and, iv) at least one water-soluble or water-dispersible fluoroacid or a salt thereof, wherein said fluoroacid is defined by the following general empirical formula (II):

$$H_p T_q F_r O_s \quad (II)$$

wherein: each of q and r represents an integer from 1 to 10; each of p and s represents an integer from 0 to 10; and, T represents an element selected from the group consisting of Ti, Zr, Hf, Si, Sn, Al, Ge, and B.

18 Claims, No Drawings

(56) References Cited

FOREIGN PATENT DOCUMENTS

| | | | |
|---|---|---|---|
| GN | 102317391 | A | 1/2012 |
| JP | 2005023372 | A | 1/2005 |
| JP | 2013032554 | A | 12/2013 |
| NO | 0120058 | A1 | 3/2001 |
| RU | 2179198 | C2 | 2/2002 |
| WO | 9421842 | A1 | 9/1994 |
| WO | 2006076197 | A1 | 7/2006 |
| WO | 2008037236 | A1 | 4/2008 |
| WO | 2015036124 | A1 | 3/2015 |
| WO | 2015036125 | A1 | 3/2015 |

* cited by examiner

PASSIVATION COMPOSITION BASED ON MIXTURES OF PHOSPHORIC AND PHOSPHONIC ACIDS

FIELD OF THE INVENTION

The present invention is directed to aqueous, acidic passivation compositions comprising both phosphoric acid and at least one water-soluble polyphosphonic acid. More particularly, the invention is directed to aqueous, acidic passivation compositions that are characterized as being free of hexavalent chromium and free of peroxide and persulphate compounds.

BACKGROUND OF THE INVENTION

The coating or plating of base metal substrates with a metal, such as zinc or aluminum, in order to provide both a decorative finish and/or corrosion protection to that base metal substrate, is long established in the art. The standards of quality control for coated and plated substrates can, of course, be demanding and consumers will therefore closely scrutinize the finish and appearance of the treated surface. Having regard to protective coatings based on zinc and zinc alloys, a surface condition known as "wet storage stain" can be unsightly and can impair the further painting or coating of the substrate. This stain, which is also known as "white rust" or "black rust" (for Galvalume® coatings) is attributable to the formation of zinc oxide and zinc hydroxide and develops upon exposure of the deposited zinc or zinc alloy to atmospheric oxygen and moisture.

Techniques to obviate wet storage stain on newly galvanized substrates are known and include inter alia: the application of duplex or powder coatings; the application of waxes and oil, particularly for base metal substrates in the forms of sheets, beams and wires; and, passivation treatments. The present invention is concerned with the treatment of zinc coatings or plating with passivation compositions which, in addition to providing corrosion resistance, can provide a variety of color coatings-including blue, yellow, olive or black—and an effective base for subsequent dyeing and coating operations.

Historically, passivation compositions have been based upon acidic aqueous solutions of chromate salts. Upon applying an acidic chromate passivation solution to a zinc coated or plated substrate, surface zinc atoms are oxidized to form, in effect, an interfacial layer of hydrated basic chromium chromate ($Cr_2O_3CrO_3 \cdot xH_2O$) and hydrous oxides of both chromium and zinc. As the acid is consumed in the oxidation reaction, however, the pH at the surface-liquid interface increases: this diminishes the combining power of chromium in the aqueous phase and leads to the precipitation of a thin gelatinous film comprising chromium hydroxide and complexes of chromium ions and zinc. This film builds up until acid protons can no longer contact the zinc metal and the surface redox reactions are thereby stopped: the resulting gel-like film may then be permitted to harden.

Traditionally, hexavalent chromium ($Cr^{6+}$ or chromium (VI)) was used in passivation compositions to supply the chromium present in the passivation film or conversion coating. However, the toxicological properties of chromium (VI) are problematic and the use of chromium (VI)-containing passivation treatments has been strongly limited by inter alia EC directive 2000/53/EC. Consequently, there has been some focus in the art on the treatment of zinc surfaces with passivation compositions in which the chromium is at least partly in the trivalent state: mention in this regard may be made of the timeworn disclosures of: U.S. Pat. Nos. 2,559,878; 3,932,198; 3,647,569; 3,501,352; 4,359,345; 4,359,346; 4,359,347; 4,359,348; 4,349,392; 4,367,099; German Patent No. DE 2526832; and, UK Patent No. GB 1,461,244. The Cr (III), as used in these citations, is not toxic and the concomitant waste removal of Cr (III) is not as expensive as that of hexavalent chromium.

Chromium (III) passivate compositions as described in the aforementioned patents nearly invariably employ peroxide-type oxidizing agents, such as $H_2O_2$, a necessary bath constituent. These and like oxidizing agents, such a persulphates, can promote some conversion of trivalent chromium to hexavalent chromium during the formation of the conversion coating. A further problem associated therewith is the high rate of consumption and loss of the peroxide or persulphate oxidizing agent which necessitates their frequent replenishment and moreover a careful control of the pH of the composition to obviate concomitant rise in pH. The consumption of peroxide (and persulphate) compounds is due in part to the presence of various activating metal ions-present in the solution as additives or contaminants-which tend to catalyze decomposition of the oxidizing agent. The frequent replenishment of the peroxide and persulphate compounds represents an economic and energetic cost to the performance of the passivation or conversion process.

Certainly, passivation compositions based on chromate (III) which do not employ peroxide or persulphate-type oxidizing agents are known in the art. For example, U.S. Pat. No. 4,578,122 A (Crotty) describes an aqueous acidic peroxide-free solution which is utilized in a process for treating receptive metal surfaces to impart a chromium passivate film thereon. The described aqueous solution contains: chromium ions, substantially all of which are present in the trivalent state; hydrogen ions to provide a pH of about 1.2 to about 2.5; at least one additional metal ion selected from the group consisting of iron, cobalt, nickel, molybdenum, manganese, lanthanum, cerium and lanthanide, said ion(s) being present in an amount effective to activate the formation of the chromate passivate film; and, nitrate ions as the essential oxidizing agent, said nitrate ions being present in an amount to provide a molar ratio of nitrate ions to the sum of chromium ions and activating metal ions of at least 4:1. The amount of nitrate ions should further be sufficient to activate the hydrated trivalent chromium to form a chromate film on the substrate. The aqueous acidic solution can optionally further contain controlled amounts of: sulfate ions; halide ions; organic carboxylic acids; a bath soluble and compatible silicate compound; and, at least one wetting agent.

The presence of nitrate salts in the composition of U.S. Pat. No. 4,578,122 is considered highly disadvantageous. Such salts are converted to NOx during the spontaneous decomposition or the intended oxidation activity, and this NOx diffuses into the atmosphere as a pollutant.

There would evidently be a benefit to developing passivation compositions that are free from either chromate (VI) or chromate (III) salts and any deleterious additive compounds: certain authors have indeed focused upon this. U.S. Pat. No. 6,203,854 (Affinito), for instance, describes a method for protecting a metal substrate from corrosion, said method comprising the steps of providing a metal substrate and applying a treatment solution to the surface of the metal substrate, wherein the treatment solution comprises a partially hydrolyzed aminosilane and a fluorine-containing inorganic compound. CN102317391 (Momentive Performance Materials Inc.) describes a passivation composition for the treatment of steel, zinc-coated steels, or aluminum, said composition being an aqueous solution of a silane compound and a silicon-based polyether copolymer. And WO01/20058 A (Henkel Corporation et al) describes a chromium-free liquid, passivation composition that contains: (a) at least one resin selected from a group consisting of urethane resins, epoxy resins, and acrylic resins; (b) at least on silane coupling agent; and, (c) dispersed solid particles with a mean particle diameter of 1 micron or less.

Unfortunately, passivation compositions based on silicates and silanes are expensive. Moreover, such passivation compositions can exhibit inferior corrosion resistance—as demonstrated by neutral salt spray (NSS) tests—and be destabilized by hydrolytic reactions.

There consequently remains a need in the art to develop passivation compositions in which the levels of compounds such as chromate salts, peroxides, persulphates and nitrate salts can be minimized but wherein the reduction of such compounds in such developed compositions is not compensated by a decline in the performance of the compositions.

SUMMARY OF THE INVENTION

In accordance with a first aspect of the invention there is provided an aqueous passivation composition for the treatment of zinc or zinc alloy coatings, said composition having a pH of less than 3 and comprising:
  i) phosphoric acid;
  ii) at least one water-soluble polyphosphonic acid or a water-soluble salt thereof, wherein said polyphosphonic acid has the general formula (I):

(I)

in which:
  n is at least 2; and,
  Z is a connecting organic moiety having an effective valency of n, said polyphosphonic acid being characterized in that at least two phosphonic groups are separated by an alkylene bridge having 1 or 2 carbon atoms ($C_1$-$C_2$ alkylene);
  iii) at least one divalent metal cation ($M^{2+}$); and,
  iv) at least one water-soluble or water-dispersible fluoroacid or a salt thereof, wherein said fluoroacid is defined by the following general empirical formula (II):

$$H_pT_qF_rO_s \quad (II)$$

wherein: each of q and r represents an integer from 1 to 10;
  each of p and s represents an integer from 0 to 10; and,
  T represents an element selected from the group consisting of Ti, Zr, Hf, Si, Sn, Al, Ge, and B.

In an important embodiment, which provides a highly stable, passivate film on zinc or zinc alloy coatings, there is provided an aqueous passivation composition having a pH of less than 3 comprising:
  i) phosphoric acid;
  ii) at least one water-soluble polyphosphonic acid or a water-soluble salt thereof, wherein said polyphosphonic acid is selected from the group consisting of aminotris (methylene phosphonic acid) (ATMP), 1-hydroxyethylidene-1,1-diphosphonic acid (HEDP), hexamethylene diamine tetra(methylene phosphonic acid) (HDTMP), diethylenetriamine penta (methylene phosphonic acid), diethylenetriamine penta (methylenephosphonic acid) (DTPMP) and mixtures thereof, and wherein the molar ratio of phosphonate groups to phosphoric acid ($H_3PO_4$) is in the range from 2:1 to 1:1;
  iii) at least one divalent metal cation ($M^{2+}$) is selected from the group consisting of $Mg^{2+}$, $Ca^{2+}$, $Mn^{2+}$, $Co^{2+}$, $Ni^{2+}$, $Sr^{2+}$, $Ba^{2+}$, and $Zn^{2+}$, wherein the total concentration of divalent metal cations ($M^{2+}$) is in the range from 0.01 to 1 moles/litre; and,
  iv) at least one fluoroacid selected from the group consisting of fluorotitanic acid ($H_2TiF_6$), fluorozirconic acid ($H_2ZrF_6$), fluorosilicic acid ($H_2SiF_6$), fluoroboric acid ($HBF_4$), fluorostannic acid ($H_2SnF_6$), fluorogermanic acid ($H_2GeF_6$), fluorohafnic acid ($H_2HfF_6$) and fluoroaluminic acid ($H_3AlF_6$), wherein said fluoroacid is present in an amount such that the molar ratio of phosphoric acid ($H_3PO_4$) to the metal (T) of said fluoroacid is in the range from 20:1 to 2:1.

Having regard to that important embodiment, good results have in particular been obtained when said aqueous composition meets at least one, preferably two and more preferably three of the following conditions: a) said polyphosphonic acid comprises or consists of 1-hydroxyethylidene-1,1-diphosphonic acid; b) said at least one divalent metal cation ($M^{2+}$) comprises or consists of $Mg^{2+}$; and, c) said at least one fluoroacid is selected from the group consisting of fluorotitanic acid ($H_2TiF_6$), fluorozirconic acid ($H_2ZrF_6$) and fluorosilicic acid ($H_2SiF_6$).

The aqueous composition should desirably be substantially free of peroxide or persulphate compounds. It is also considered beneficial that the composition be substantially free of nitrate compounds. And moreover, it is preferred that the passivation composition be substantially free of free fluoride anions, that is fluoride anions not bound in complex form.

In accordance with a second aspect of the invention there is provided a process for imparting a passivate film to a substrate to which a zinc or zinc alloy coating has been applied to at least one surface thereof, said process comprising contacting said at least one coated surface of the substrate with an aqueous composition as defined herein above and in the appended claims: the composition is applied at a temperature of from 20° C. to 90° C. for a period of time sufficient to form a passivate film thereon.

In accordance with a third aspect of the invention, there is provided a passivated substrate obtained by the process defined herein above and in the appended claims.

Definitions

As used herein, the singular forms "a", "an" and "the" include plural referents unless the context clearly dictates otherwise.

The terms "comprising", "comprises" and "comprised of" as used herein are synonymous with "including", "includes", "containing" or "contains", and are inclusive or open-ended and do not exclude additional, non-recited members, elements or method steps. If used, the phrase "consisting of" is closed, and excludes all additional elements. Further, the phrase "consisting essentially of" excludes additional material elements, but allows the inclusions of non-material elements that do not substantially change the nature of the invention.

When amounts, concentrations, dimensions and other parameters are expressed in the form of a range, a preferable range, an upper limit value, a lower limit value or preferable upper and limit values, it should be understood that any ranges obtainable by combining any upper limit or preferable value with any lower limit or preferable value are also specifically disclosed, irrespective of whether the obtained ranges are clearly mentioned in the context.

The words "preferred", "preferably", "particularly" and "desirably" are used frequently herein to refer to embodiments of the disclosure that may afford particular benefits, under certain circumstances. However, the recitation of one or more preferable, preferred, particular or desirable embodiments does not imply that other embodiments are not useful and is not intended to exclude those other embodiments from the scope of the disclosure.

As used throughout this application, the word "may" is used in a permissive sense—that is meaning to have the potential to—rather than in the mandatory sense.

The present compositions are defined herein as being "substantially free" of certain compounds, elements, ions or other like components. The term "substantially free" is intended to mean that the compound, element, ion or other like component is not deliberately added to the composition and is present, at most, in only trace amounts which will have no (adverse) affect on the desired properties of the coating. The term "substantially free" encompasses those embodiments where the specified compound, element, ion, or other like component is completely absent from the composition or is not present in any amount measurable by techniques generally used in the art.

As used herein, room temperature is 23° C. plus or minus 2° C.

As defined herein, the term "conversion coating" or "conversion treatment," refers to a treatment of the surface of a substrate which causes the surface material to be chemically converted to a different material. The term "passivation" refers to a treatment of the surface of a substrate to form a barrier layer to corrosive conditions on said surface but without a cohesive film forming a chemical bond between the surface and the passivation layer.

The term "passivation composition" as used herein refers to that composition which actually contacts the zinc-coated or zinc-alloy coated substrate. As is known in the art, such contacting occurs in a so-called "bath" which is shaped, sized and disposed to enable at least part of the substrate to be immersed therein. The passivation bath should moreover be sized to allow for movement of the composition around and throughout the loaded substrate, which movement can be further enhanced with recirculation and/or ultrasonics. The pH of the composition within the bath, the temperature of the bath, and contact time of the substrate are result effective variables which should be monitored either manually or automatically, whenever possible.

Viscosities of the passivation compositions may be determined using the Brookfield Viscometer, Model RVT at standard conditions of 20° C. and 50% Relative Humidity (RH). The viscometer is calibrated using silicone oils of known viscosities, which vary from 5,000 cps to 50,000 cps. A set of RV spindles that attach to the viscometer are used for the calibration. Measurements of the passivation compositions are done using the No. 6 spindle at a speed of 20 revolutions per minute for 1 minute until the viscometer equilibrates. The viscosity corresponding to the equilibrium reading is then calculated using the calibration.

As used herein, the total acidity of the passivation composition means that mass of potassium hydroxide (KOH) in milligrams that is required to neutralize one gram of the composition. According to a typical measurement procedure for total acidity, a known amount of the composition is provided and titrated with a solution of potassium hydroxide (KOH) of known concentration using phenolphthalein as a color indicator.

Unless otherwise stated, where a molar ratio is given herein with respect "to metal", this refers to the total content of metal in the composition, independent of the oxidation state(s) of that metal.

As used herein, the term "alloy" refers to a substance composed of two or more metals or of a metal and a non-metal which have been intimately united, usually by being fused together and dissolved in each other when molten. The term "zinc alloy" therefore denotes an alloy of which zinc metal is a constituent component, which zinc will generally comprise at least 40 wt. %-more typically at least 50 wt. % or at least 60 wt. %—of the alloy, on a metals basis. Metals which may be alloyed with zinc include, but are not limited to, aluminum, tin, nickel, titanium and cobalt.

Herein, for a zinc/aluminum alloy, it is preferred that zinc constitutes, on a metals basis, at least 40 wt. % of the alloy and conversely that aluminum constitutes, on a metals basis, up to 60 wt. % of the alloy. For a zinc/tin alloy, it is preferred that zinc constitutes, on a metals basis, at least 70 wt. % and more particularly at least 80 wt. % of the alloy and conversely that tin constitutes, on a metals basis, up to 30 wt. % and more particularly up to 20 wt. % of the alloy.

Herein, for a zinc/titanium alloy, it is preferred that zinc constitutes, on a metals basis, at least 85 wt. % and more particularly at least 90 wt. % of the alloy and conversely that titanium constitutes, on a metals basis, up to 15 wt. % and more particularly up to 10 wt. % of the alloy. For a zinc/nickel alloy, it is similarly preferred that zinc constitutes, on a metals basis, at least 85 wt. % and more particularly at least 90 wt. % of the alloy and conversely that nickel constitutes, on a metals basis, up to 15 wt. % and more particularly up to 10 wt. % of the alloy. For a zinc/cobalt alloy, it is preferred that zinc constitutes, on a metals basis, at least 95 wt. % of the alloy and conversely that cobalt constitutes, on a metals basis, up to 5 wt. % of the alloy.

As used herein, "phosphoric acid" refers to ortho-phosphoric acid having the formula $H_3PO_4$, which acid is typically available as an aqueous solution having a concentration up to 75 wt. % $H_3PO_4$. As used herein "phosphonic acid" refers to the phosphorus oxoacid having the formula $H_3PO_3$ that consists of a single pentavalent phosphorus covalently bound via single bonds to a single hydrogen and two hydroxy groups and via a double bond to an oxygen.

As used herein, the term "α-hydroxycarboxylic acid" means a carboxylic acid having at least one hydroxyl functional group occupying an α-position on said acid (carbon adjacent to a carboxylic acid functional group). The presence of hydroxyl groups occupying positions in the molecule other than the α-position on said acid is not precluded. This α-hydroxycarboxylic acid is included in the present composition in the form of the free acid.

The term "hydrocarbyl group" is used herein in its ordinary sense, which is well-known to those skilled in the art.

As used herein, the term "$C_6$-$C_{10}$ aryl group" refers to an aromatic monocyclic or multicyclic ring system of 6 to 10 carbon atoms. The "aryl group" may optionally be substituted with one or more $C_1$-$C_{12}$ alkyl, alkylene, alkoxy, or haloalkyl groups. Exemplary aryl groups include phenyl or naphthyl, or substituted phenyl or substituted naphthyl.

Unless otherwise indicated, the term "alkyl", as used herein, includes straight chain moieties, and where the number of carbon atoms suffices, branched moieties. The alkyl group may optionally be substituted. As such, the term "$C_1$-$C_4$ alkyl" includes saturated straight chain and branched alkyl groups having from 1 to 4 carbon atoms. Examples of $C_1$-$C_4$ alkyl groups include methyl, ethyl, propyl, isopropyl, butyl, isobutyl and tert-butyl.

The terms "alkylene group" refers to a group that are radicals of a linear, branched or cyclic alkane, which group may be substituted or unsubstituted and may optionally be interrupted by at least one heteroatom.

As used herein, "$C_2$-$C_6$ alkenyl" group refers to an aliphatic carbon group that contains 2 to 6 carbon atoms and at least one double bond disposed in any position. Like the aforementioned alkyl group, an alkenyl group can be straight or branched, and may optionally be substituted. The term "alkenyl" also encompasses radicals having "cis" and "trans" configurations, or alternatively, "E" and "Z" configurations, as appreciated by those of ordinary skill in the art. In general, however, a preference for unsubstituted alkenyl groups containing from 2 to 6 ($C_2$-$C_6$) or from 2 to 4 ($C_2$-$C_4$) carbon atoms should be noted. And Examples of $C_2$-$C_6$ alkenyl groups include, but are not limited to: ethenyl; 1-propenyl; 2-propenyl; 1-methyl-ethenyl; 1-butenyl; 2-butenyl; 4-methylbutenyl; 1-pentenyl; 2-pentenyl; 3-pentenyl; 4-pentenyl; 4-methyl-3-pentenyl; 1-hexenyl; 3-hexenyl; and, 5-hexenyl.

The term "$C_3$-$C_6$ cycloalkyl" as used herein means an optionally substituted, saturated cyclic hydrocarbon having 3-6 carbon atoms. Exemplary cycloalkyl groups include cyclopropyl, cyclobutyl, cyclopentyl or cyclohexyl groups.

The term "alkoxy", as used herein, means "—O-alkyl" or "alkyl-O—", wherein "alkyl" is defined as above.

The term "substituted" refers to substitution with at least one suitable substituent. For completeness: the substituents may connect to the specified group or moiety at one or more positions; and, multiple degrees of substitution are allowed unless otherwise stated. Further, the terms "substitution" or "substituted with" include the implicit proviso that such substitution is in accordance with permitted valence of the substituted atom and the substituent, and that the substitution results in a stable compound that does not spontaneously undergo transformation by, for instance, rearrangement, cyclization or elimination.

Having regard to the α-hydroxycarboxylic acid defined above and hereinbelow, substitution(s) of the group $R_1$ will conventionally be selected from the group consisting of: halogen; oxo; —OH; and, —COOH.

Where mentioned, the expression "interrupted by at least one heteroatom" means that the main chain of a residue comprises, as a chain member, at least one atom that differs from carbon atom. More particularly the term "heteroatom" refers to nitrogen, oxygen, halogens, phosphorus or sulfur. Oxygen (O) and nitrogen (N) may be mentioned as typical heteroatoms in the context of the present invention.

DETAILED DESCRIPTION OF THE INVENTION

The Passivation Composition
Component (i)

The composition comprises by necessity phosphoric acid. The added amount thereof is that required to adjust the pH of the passivation composition to a value of less than 3, in particular to a pH of from 1 to 3 or from 1.2 to 2.8.
Component (ii)

A second required component of the composition of the present invention is constituted by at least one water-soluble polyphosphonic acid or a water-soluble salt thereof, wherein said polyphosphonic acid has the general formula (I):

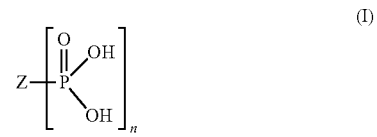

in which:

n is at least 2; and,

Z is a connecting organic moiety having an effective valency of n, said polyphosphonic acid being characterized in that at least two phosphonic groups are separated by an alkylene bridge having 1 or 2 carbon atoms ($C_1$-$C_2$ alkylene).

In particular embodiments, n is an integer from 2 to 5 or, preferably, either 2 or 3. Most desirably, said polyphosphonic acid is selected from a group consisting of aminotris (methylene phosphonic acid) (ATMP); 1-hydroxyethylidene-1,1-diphosphonic acid (HEDP); hexamethylene diamine tetra(methylene phosphonic acid) (HDTMP); diethylenetriamine penta (methylene phosphonic acid); diethylenetriamine penta (methylenephosphonic acid (DTPMP); and, mixtures thereof. A particular preference for the use of 1-hydroxyethylidene-1,1-diphosphonic acid (HEDP) should be noted.

Suitable water soluble salts of the aforementioned polyphosphonic acids include the sodium, potassium, calcium, magnesium, ammonium, triethanolammonium, diethanolammonium and monoethanolammonium salts.

The polyphosphonic acids or the water soluble salts thereof are preferably included in the compositions in an amount such that the molar ratio of phosphonate groups to phosphoric acid ($H_3PO_4$) in the composition is in the range from 2:1 to 1:1, more preferably in the range from 1.75:1 to 1.25:1 and most preferably from 1.6:1 to 1.4:1. Compositions meeting these molar ratio conditions have been found to be effective and stable without promoting substantial etching of the coated substrates to which they are applied.

Component (iii)

The passivation composition further contains at least one divalent metal cation ($M^{2+}$). In preferred embodiments, said at least one divalent metal cation (M) is selected from the group consisting of: $Mg^{2+}$; $Ca^{2+}$; $Mn^{2+}$; $Co^{2+}$; $Ni^{2+}$; $Sr^{2+}$; $Ba^{2+}$; and, $Zn^{2+}$. The foregoing metal ions or mixtures thereof are most conveniently introduced into the composition as metal oxides, metal hydroxides and/or soluble and compatible metal salts, including but not limited to sulfate and halide salts. The use of nitrate and fluoride salts for this purpose is not preferred, however.

In a preferred embodiment of the present invention, the passivation composition comprises magnesium ($Mg^{2+}$). This magnesium is desirably introduced into the aqueous passivation composition as one or more of: magnesium oxide, magnesium hydroxide; magnesium sulphate; and, magnesium chloride. A particular preference for magnesium oxide or magnesium hydroxide may be noted.

The total molar concentration of the divalent metal cations ($M^{2+}$) in the aqueous composition is conventionally in the range from 0.01 to 1 moles/litre but more typically is from 0.01 to 0.5 moles/litre.

Component (iv)

In accordance with the present invention, the passivation composition comprises at least one water-soluble or water-dispersible fluoroacid or a salt thereof, wherein said fluoroacid is defined by the following general empirical formula (II):

$$H_pT_qF_rO_s \qquad (II)$$

wherein: each of q and r represents an integer from 1 to 10; each of p and s represents an integer from 0 to 10; and, T represents an element selected from the group consisting of Ti, Zr, Hf, Si, Sn, Al, Ge, and B.

Preferred fluoroacids of empirical formula (II) include compounds where: T is selected from Ti, Zr, or Si; p is 1 or 2; q is 1; r is 2, 3, 4, 5 or 6; and, s is 0, 1, or 2.

Exemplary fluoroacids used in the process of the invention may be selected from the group consisting of: fluorotitanic acid ($H_2TiF_6$); fluorozirconic acid ($H_2ZrF_6$); fluorosilicic acid ($H_2SiF_6$); fluoroboric acid ($HBF_4$); fluorostannic acid ($H_2SnF_6$); fluorogermanic acid ($H_2GeF_6$); fluorohafnic acid ($H_2HfF_6$); and, fluoroaluminic acid ($H_3AlF_6$); Preferred fluoroacids are: fluorotitanic acid ($H_2TiF_6$); fluorozirconic acid ($H_2ZrF_6$); and, fluorosilicic acid ($H_2SiF_6$).

Subject to the condition that the salt is water-soluble or water dispersible, one or more of the H atoms of the aforementioned fluoroacids may be replaced by suitable cations, such as ammonium, alkaline earth metal cations or alkali metal cations. The salts of alkali metal cations and ammonium are preferred in this context and mention may therefore be made of the following examples of suitable fluoroacid salts: $(NH_4)_2ZrF_6$; $H(NH_4)ZrF_6$; $(NH_4)_2TiF_6$; $H(NH_4)_2TiF_6$; $Na_2ZrF_6$; $K_2ZrF_6$; $Li_2ZrF_6$; $Na_2TiF_6$; $K_2TiF_6$; and, $Li_2TiF_6$.

Such salts may be added directly to the composition or may be produced in situ in the aqueous passivation composition by the partial or full neutralization of the acid fluoride or acid oxyfluoride with an appropriate base. It is noted that said base may be organic or inorganic in character: ammonium bicarbonate and hydroxylamine might be used, for instance.

The fluoroacid or salt thereof is typically included in the composition such that the molar ratio of phosphoric acid ($H_3PO_4$) to the metal (T) of said fluoroacid is in the range from 20:1 to 2:1, preferably from 12:1 to 3:1 and more preferably 10:1 to 4:1. When the level of phosphoric acid is outside the above ranges, the stability of the formulation is diminished: at lower levels of phosphoric acid within the stated ranges, the concomitant loss of stability of the formulation can be mitigated by increasing the amount of divalent metal cations in the composition. When the level of metal (T) falls below the stated molar ranges, the stability of the composition may be substantively affected but a decline in performance in the neutral salt spray (NSS) may be observed.

In an alternative but not mutually exclusive expression, the fluoroacid or salt thereof should be included in the passivation composition such that the molar concentration of the metal (T) in the aqueous composition is conventionally in the range from 0.1 to 1 moles/litre but more typically is from 0.2 to 0.8 moles/litre.

Adjunct Ingredients

The presence of other complex fluoride anions in the passivation composition is not precluded and mention in this regard may be made of: fluoroindates (e.g. $InF_4^{-1}$); fluorophosphates (e.g. $PF_6^{-1}$); fluoroarsenates (e.g. $AsF_6^{-1}$); fluoroantimonates (e.g. $SbF_6^{-1}$); fluorobismuthates (e.g. $BiF_6^{-1}$); fluoro sulfates (e.g. $SF_6^{-2}$); fluoroselenates (e.g. $SeF_6^{-2}$); fluorotellurates (e.g. $TeF_6^{-2}$ or $TeOF_5^{-1}$); fluorocuprates (e.g. $CuF_3^{-1}$); fluoroargentates; fluorozincates (e.g., $ZnF_4^{-2}$); fluorovanadates (e.g. $VF^{-2}$); fluoroniobates (e.g. $NbF^{-2}$); fluorotantalates (e.g. $TaF_7^{-2}$); fluoromolybdates (e.g. $MoF_6^{-3}$); fluorotungstates (e.g. $WF_6^{-1}$); fluoroyttrates (e.g. $YF_6^{-3}$); fluorolanthanates (e.g. $LaF_6^{-3}$); fluorocerates (e.g. $CeF_6^{-3}$ or $CeF_6^{-2}$); fluoromanganates (e.g. $MnF_6^{-2}$); fluoroferrates (e.g. $FeF_6^{-3}$); fluoronickelates; and fluorocobaltates. Such anions may be included in the form of water-soluble or water dispersible salts, in particular the ammonium, alkaline earth metal or alkali metal salts.

When present, said complex fluoride anions should be included in the composition in an amount up to 0.1 moles/litres, for example up to 0.05 moles/litre.

The presence in the passivation composition of free fluoride ions—not bound in complex form—is also not precluded as the fluoride anions can act as accelerators in the formation of passivation coatings and are present at the interface between the conversion coating and the metal matrix. Such free fluoride anions can be included through the addition to the passivation compositions of, for example: hydrofluoric acid; alkali metal fluorides, such as sodium fluoride; alkali metal hydrogen fluorides, such as sodium hydrogen fluoride; ammonium fluoride; and, ammonium hydrogen fluoride.

This aside, the presence of free fluoride ions—not bound in complex form—is not preferred. Despite the utility of the fluoride species in the passivation compositions, the environmental release of fluoride is problematic as documented in https://www.cdc.gov/niosh/. Thus, it is preferred that the passivation composition be substantially free of free fluoride anions.

In addition to the aforementioned phosphoric acid, the passivation compositions may comprise one or more further mineral acids: the use of nitric acid is not precluded but is not preferred; conversely, the addition of phosphonic or sulphuric acid is considered to be particularly suitable. The above recited pH of the passivation composition is somewhat determinative of the added amount of such acid(s). Within that pH constraint, the presence of phosphonate or sulphate ions in the treatment bath in concentrations of up to 5% by weight and, more particularly, between 0.1 and 3% by weight can be advantageous.

The composition of the present invention may optionally comprise at least one α-hydroxycarboxylic acid represented by the general formula (III): $R_1CH(OH)COOH$ (III) wherein: $R_1$ represents a hydrogen atom, a $C_1$-$C_4$ alkyl group, a $C_2$-$C_6$ alkenyl group, a $C_1$-$C_6$ alkoxy group, a $C_3$-$C_6$ cycloalkyl group or a $C_6$-$C_{10}$ aryl group.

Suitable α-hydroxycarboxylic acids include but are not limited to: glycolic acid; lactic acid (2-hydroxypropanoic acid); 2-hydroxybutanoic acid; 2-hydroxypentanoic acid; 2-hydroxyhexanoic acid; glucuronic acid; citric acid; mandelic acid; galacturonic acid; ribonic acid (2,3,4,5-tetrahydroxypentanoic acid); gluconic acid (2S,3S,4R,5S)-2,3,4,5,6-pentahydroxyhexanoic acid; tartronic acid; tartaric acid; and, malic acid.

In a preferred embodiment, said at least one α-hydroxycarboxylic acid is selected from the group consisting of: glycolic acid; gluconic acid; lactic acid (2-hydroxypropanoic acid); 2-hydroxybutanoic acid; 2-hydroxypentanoic acid; and, 2-hydroxyhexanoic acid. More particularly, the α-hydroxycarboxylic acid(s) of the coating composition should comprise or consist of gluconic acid.

For completeness, it is again noted that the above recited pH of the passivation composition is somewhat determinative of the added amount of such α-hydroxycarboxylic acid(s). When added within that pH constraint, the α-hydroxycarboxylic acid(s) should conventionally be included in the aqueous passivation composition in an amount up to 0.1 moles/litres, for example up to 0.05 moles/litre.

It is considered that the corrosion-protection performance of the disclosed passivation compositions—and resulting passivate films—can be enhanced by the incorporation of a transition metal salt and/or a transition metal complex therein. Considered particularly useful in this regard are the salts or complexes of transition metals selected from the group consisting of Ce, Ni, Co, V, Fe, Zn, Zr, Mn, Mo, W, Ti, Zr, Hf, Bi and the lanthanides.

Whilst said transition metals may be present in the complex fluoride anions mentioned hereinabove, such transition metals may alternatively or additionally be included in the composition as complexes with other ligands and/or as salts with further anions, provided said salts are at least partially soluble in water. As examples of anions, there may be mentioned: oxide; hydroxide; sulphate; chloride; iodide; citrate; lactate; succinate; formate; oxalate; malonate; and, acetate. As exemplary ligands for transition metal complexes, there may be mentioned: ethylenediaminetetraacetic acid (EDTA); diethylenetriaminepentaacetic acid (DTPA); hydroxyethylethylenediaminetriacetic acid (HEDTA); nitrilotriacetic acid (NTA); and, methylglycinediacetic acid (MGDA).

The present compositions may further comprise additives which are conventional in this field; in particular, the compositions might comprise: corrosion inhibitors, such as dialkylthioureas, cupric sulphate and copper sulphate; adhesion promoters; non-ionic surfactants; wetting agents; defoaming agents; sequestrants; lubricants; and, mixtures thereof. As further exemplary corrosion inhibitors mention may be made of the following commercial materials: the Rodine® series, available from JMN Specialties, Inc. and Henkel Corporation; the Dodicor® series, available from Clariant AG; and, the Armohib® series available from Akzo Nobel Surfactants LLC. That aside, any such additives are necessarily minor ingredients of the present compositions and, when used, should only be used in amounts which are not deleterious to the performance of the composition and the coating derived there from.

Exemplary Formulation of the Passivation Compositions

In an exemplary embodiment, which embodiment is not intended to be limiting of the present invention, there is provided an aqueous passivation composition having a pH of less than 3, said composition comprising:
  i) phosphoric acid;
  ii) 1-hydroxyethylidene-1,1-diphosphonic acid (HEDP) such that the molar ratio of phosphonate groups to phosphoric acid ($H_3PO_4$) is in the range from 2:1 to 1:1;
  iii) $Mg^{2+}$ and optionally at least one further divalent metal cation ($M^{2+}$) selected from the group consisting of $Ca^{2+}$, $Mn^{2+}$, $Co^{2+}$, $Ni^{2+}$, $Sr^{2+}$, $Ba^{2+}$, and $Zn^{2+}$, wherein the total concentration of divalent metal cations ($M^{2+}$) is in the range from 0.01 to 1 moles/litre; and,
  iv) at least one fluoroacid selected from the group consisting of fluorotitanic acid ($H_2TiF_6$), fluorozirconic acid ($H_2ZrF_6$) and fluorosilicic acid ($H_2SiF_6$), wherein said fluoroacid is present in an amount such that the molar ratio of phosphoric acid ($H_3PO_4$) to the metal (T) of said fluoroacid is in the range from 20:1 to 2:1.

In a further exemplary embodiment, which embodiment is again not intended to be limiting of the present invention, there is provided an aqueous passivation composition having a pH of less than 3, said composition comprising:
  i) phosphoric acid;
  ii) 1-hydroxyethylidene-1,1-diphosphonic acid (HEDP) such that the molar ratio of phosphonate groups to phosphoric acid ($H_3PO_4$) is in the range from 1.6:1 to 1.4:1;
  iii) $Mg^{2+}$ and optionally at least one further divalent metal cation ($M^{2+}$) selected from the group consisting of $Ca^{2+}$, $Mn^{2+}$, $Co^{2+}$, $Ni^{2+}$, $Sr^{2+}$, $Ba^{2+}$, and $Zn^{2+}$, wherein the total concentration of divalent metal cations ($M^{2+}$) is in the range from 0.01 to 0.5 moles/litre; and,
  iv) at least one fluoroacid selected from the group consisting of fluorotitanic acid ($H_2TiF_6$), fluorozirconic acid ($H_2ZrF_6$) and fluorosilicic acid ($H_2SiF_6$), wherein said fluoroacid is present in an amount such that the molar ratio of phosphoric acid ($H_3PO_4$) to the metal (T) of said fluoroacid is in the range from 10:1 to 4:1.

Preparation of the Passivation Compositions

The aqueous passivation compositions are formulated by simple mixing of the various components. If necessary, the passivation composition may be prepared well in advance of its application. However, in an interesting alternative embodiment, a concentrated passivation composition may first be obtained by mixing components with only a fraction of the water that would be present in the passivation composition as applied: the concentrated passivation composition may then be diluted with the remaining water shortly before its introduction into the passivation bath. It is considered that such concentrated passivation compositions may be prepared and stored as either single-package concentrates—that can be converted by dilution with water only—or as multi-part concentrates, two or more of which must be combined and diluted to form a complete working composition according to the invention. Any dilution can be effected simply by the addition of water, in particular deionized and/or demineralized water, under mixing. The passivation composition might equally be prepared within a rinse stream whereby one or more streams of the concentrate(s) is injected into a continuous stream of water.

Without specific intention to limit the amount of water included in the passivation compositions, it is preferred that said compositions contain from 40 to 90 wt. %, more preferably from 50 to 80 wt. %, based on the weight of the composition, of water. In an alternative but not mutually exclusive characterization, the passivation composition may be defined by a viscosity of from 0.005 to 1 Pa·s (50 cps to 1000 cps), as measured using a Brookfield viscometer at 25° C.

Methods and Applications

Whilst the present invention is concerned with passivating of surfaces of zinc or zinc alloys, there is no intention to limit the base substrate to which that zinc or zinc alloy may have been applied nor the method of such application. As such, suitable base metal substrates may include but not be limited to iron, nickel, copper, aluminium and alloys thereof. Such metals and alloys may be provided in various forms, including sheets, plates, cuboids, spheres, solid cylinders, tubes and wires. Moreover, the plating or coating of zinc or zinc alloy may be applied to such base substrates by: electroplating; galvanizing, including hot-dip galvanizing and thermal diffusion galvanizing; and, galvannealing. By way of example only, the passivation compositions and methods of the present invention may have utility in the treatment of: GALVALUME®, a 55% Al/43.4% Zn/1.6% Si alloy coated sheet steel available from Bethlehem Steel Corporation; and, GALFAN®, a 5% Al/95% Zn alloy coated sheet steel available from Weirton Steel Corporation.

In accordance with process aspects of the present invention, it is often advisable to remove foreign matter from the coated or plated metal substrate by cleaning and degreasing the relevant surfaces. Such treatments are known in the art and can be performed in a single or multi-stage manner constituted by, for instance, the use of one or more of: a waterborne alkaline degreasing bath; a waterborne cleaning emulsion; a cleaning solvent, such as carbon tetrachloride or trichloroethylene; and, a water rinse, preferably of deionized or demineralized water. In those instances where a waterborne alkaline degreasing bath is used, any of the degreasing agent remaining on the surface should desirably be removed by rinsing the substrate surface with deionized or demineralized water. Irrespective of the cleaning or degreasing agent applied, the so-treated substrate should not be subjected to an intermediate drying step prior to either the passivation treatment or to any subsequent pre-treatment step which precedes said passivation treatment.

As therefore intimated above, the present invention does not preclude the pre-treatment of the zinc or zinc alloy surface, independently of the performance of cleaning and/or degreasing steps. Such pre-treatments are known in the art and reference in this regard may be made to: German Patent Application No. DE 197 33 972 A1; German Patent Application No. DE 10 2010 001 686 A1; German Patent Application No. DE 10 2007 021 364 A1; and, US Patent Application Publication No. 2014/360630.

After said cleaning, degreasing and/or pre-treatment steps, an operating bath as hereinbefore described is prepared and the passivation composition is applied to the substrate by, without limitation, immersion, flooding, air-atomized spraying, air-assisted spraying, airless spraying, high-volume low-pressure spraying and air-assisted airless spraying. The minimum contact time of the composition with the substrate is most broadly that time which is sufficient to form the desired passivate film thereon: that contact time can be as little as 1 second or as great as 15 minutes in that instance where the passivation or conversion treatment is being performed on metal that will be cold worked: however, dependent upon the pH and the concentration of the applied solution, a contact time of from 5 to 300 seconds, for example from 5 to 50 seconds, would be more typical. Moreover, the compositions are applied at a temperature ranging from 20° C. to 90° C., for instance from 30° C. to 80° C. or from 40° C. to 70° C.

At the conclusion of the passivation treatment, the article is extracted from the bath and dried using, for instance, ambient air drying, circulating warm air, forced air drying or infrared heating. It is not precluded that the article be subjected to: at least one water rinse to remove residual passivation composition therefrom; and/or, rinsing with a dilute silicate solution based on the aforementioned silicate compounds and having a temperature of from 20° C. to 70° C. The silicate compound can be present in the rinse solution in an amount of from 1 to 40 g/l, for example from 5 to 15 g/l, calculated as $SiO_2$. The rinsed substrate may be dried after completion of the rinsing step(s) or, if applicable, after each rinse solution.

The composition according to the present invention yields a passivate film that is either colorless, or blue or olive in color, with a flat to glossy finish. The exact nature of that finish is determined predominantly by the base substrate, the zinc or zinc alloy coating, and the immersion time in the conversion coating composition. Zinc or zinc alloy coatings passivated in accordance with the present invention exhibit corrosion protection to 50-96 hours before the observed onset of white rust corrosion, as defined by ASTM B-201. Alternatively or additionally, said zinc or zinc alloy coatings passivated in accordance with the present invention exhibit corrosion protection to 50-96 hours before the observed onset of white rust corrosion (as defined by ASTM B-201) when treated with neutral salt spray (NSS, 5 wt. % NaCl, 95 wt. % $H_2O$) under steady state conditions in accordance with the procedure of ASTM B-117.

The present invention does not preclude supplementary conversion coatings being applied to the passivate film obtained in accordance with the present invention; indeed such supplementary coatings may further extend corrosion protection and improve the aesthetics of the finished article. Inorganic coatings based on silicates and organic conversion coatings based on epoxy resins might be mentioned as non-limiting examples of supplemental conversion coatings: reference in this regard may be made to inter alia U.S. Pat. No. 5,743,971 (Inoue) and U.S. Pat. No. 5,855,695 (McMillen). These supplemental conversion coatings may be applied by any suitable means known in the art, such as by dipping, spraying, electro-coating or powder coating.

The conversion coating(s) may constitute the topcoat applied to the substrate surface. Alternatively, the conversion coating(s) may serve: as an undercoat for paints, lacquers, inks or powder coatings; as a base to which polymers, such as rubber, may be bound; and/or, as a base to which adhesives or sealants may be applied.

Various features and embodiments of the disclosure are described in the following examples, which are intended to be representative and not limiting.

EXAMPLES

The following commercial products are used in the Reference Examples and Example according to the invention:
Codex 661:1-Hydroxyethylidene-1,1-diphosphonic acid (CAS No. 2809-21-4) available from Excel Industries Limited.
TD-1355-HM: Polymer resin available from Henkel Surface Technologies PVT Ltd.
Fluotitanic Acid: Hexaflurorotitanic acid ($H_2TiF_6$) available S.B. Chemicals.

Aqueous passivation compositions were prepared by mixing the ingredients given in Table 1 herein below:

TABLE 1

| | Composition (g) | | |
| --- | --- | --- | --- |
| Ingredient | Reference Example 1 | Reference Example 2 | Example 1 |
| Water | 40.7 | 86.0 | 67.5 |
| Phosphoric acid (85%) | 15.6 | 6.0 | 10.0 |
| 1-Hydroxyethylidene-1,1-Diphosphonic Acid (60%) | 0 | 6.0 | 15.0 |
| Chromic acid ($H_2CrO_4$) | 7.8 | 0 | 0 |
| Chromium nitrate ($Cr(NO_3)_3$) | 25.0 | 0 | 0 |
| TD-1355-HM | 10 | 0 | 0 |
| Magnesium Oxide (MgO) | 0 | 0 | 2.5 |
| Vanadium Oxide ($V_2O_5$) | 0 | 2 | 0 |
| Fluotitanic Acid (50%) | 0 | 0 | 5 |
| Gluconic acid (50%, Technical Grade) | 4.0 | 0 | 0 |

Based on these tabulated aqueous compositions, the following tests were performed.

Specific Gravity: The specific gravity of the aqueous compositions was measured in accordance with ASTM D891-18.

Standard Test Panel Preparation: Specimens of Advanced Coating Technology (ACT) G-90 hot dipped galvanized steel were mechanically cut into squares of 4 cm×4 cm dimensions. Each obtained panel was treated with an alkaline cleaner at 55° C. for 10 seconds, rinsed with tap water at room temperature and then dried by squeegeeing. The panels were then separately coated with a defined wet layer thickness of each passivation composition selected for evaluation using a Chemcoater: duplicate panels were prepared for each passivation composition. The resultant test panels coated with a wet film of the passivation composition were then dried upon heating to a peak metal temperature (PMT) of from 55-60° C. The obtained coating weight of the test panels was determined on a metals basis.

Zinc Dissolution Panel Preparation: Specimens of Advanced Coating Technology (ACT) G-90 hot dipped galvanized steel were mechanically cut into squares of 4 cm×4 cm dimensions. Each obtained panel was treated with an alkaline cleaner at 55° C. for 10 seconds, rinsed with tap water at room temperature and then dried by squeegeeing. The panels were then separately immersed for 2 hours in a bath (volume 20 ml) of each passivation composition selected for evaluation. The resultant coated test panels were then removed from the bath. To then measure the amount of zinc which was dissolved during the formation of the conversion coating, a complexometric (or chelometric) titration with EDTA (ethylenediaminetetraacteic acid) was performed on the residual aqueous composition in the bath.

Neutral salt spray (NSS): This test was carried out according to ASTM B117 with a 5% NaCl solution at 35° C. (https://www.astm.org/Standards/B117). The coated panels were disposed in the spray chamber (ERICHSEN Model 606/400 L) at 15-30° from the vertical for 96 hours. The test panels were not allowed to contact other surfaces in the chamber and condensed or corrosion products on their surfaces were not permitted to cross-contaminate each other. Photographic recording of the test panels was performed each 24 hours. After exposure, test panels were rinsed in deionised water to remove salt deposits from their surface and then immediately dried. From a visual inspection of the coated panels at 96 hours: i) coated panels for which less than 5% by area showed white rust were held to have passed said test; and, ii) conversely, coated panels showing >5% by area of white rust were held to have failed said test.

The results of these tests are illustrated in Table 2 herein below.

TABLE 2

| Test Parameters | Reference Example 1 | Reference Example 2 | Example 1 |
|---|---|---|---|
| Appearance | Dark green | Clear blue | Colorless |
| pH (25% v/v bath) | 0.3 | | 2.3 |
| Total Acidity of Composition (mg/g KOH) | 27 | | 30.6 |
| Specific Gravity | 1.26 | | 1.15 |
| Composition Stability at pH 8.5 | Stable, no precipitation | Stable, no precipitation | Stable, no precipitation |
| Coating Weight (mg/m²) on a metals Basis | 35 | 25 | 5-8 |
| Salt Spray Tests (ASTM B117) | Pass | Fail | Pass |

In view of the foregoing description and examples, it will be apparent to those skilled in the art that equivalent modifications thereof can be made without departing from the scope of the claims.

What is claimed is:

1. An aqueous passivation composition for the treatment of zinc or zinc alloy coatings, said composition having a pH of less than 3 and comprising:
   i) phosphoric acid;
   ii) at least one water-soluble polyphosphonic acid or a water-soluble salt thereof, wherein said polyphosphonic acid has a general formula (I):

in which:
   n is at least 2; and,
   Z is a connecting organic moiety having an effective valency of n,
   said polyphosphonic acid being characterized in that at least two phosphonic groups are separated by an alkylene bridge having 1 or 2 carbon atoms ($C_1$-$C_2$ alkylene), wherein the composition has a molar ratio of phosphonate groups to phosphoric acid ($H_3PO_4$) in a range from 2:1 to 1:1;
   iii) at least one divalent metal cation ($M^{2+}$); and,
   iv) at least one water-soluble or water-dispersible fluoroacid or a salt thereof, wherein said fluoroacid is defined by general empirical formula (II):

$$H_pT_qF_rO_s \quad (II)$$

wherein: each of q and r represents an integer from 1 to 10;
   each of p and s represents an integer from 0 to 10; and,
   T represents an element selected from the group consisting of Ti, Zr, Hf, Si, Sn, Al, Ge, and B.

2. The composition according to claim 1, wherein in general formula (I) n is an integer from 2 to 5.

3. The composition according to claim 1, wherein said polyphosphonic acid is selected from the group consisting of: aminotris(methylene phosphonic acid) (ATMP); 1-hydroxyethylidene-1,1-diphosphonic acid (HEDP); hexamethylene diamine tetra(methylene phosphonic acid) (HDTMP); diethylenetriamine penta (methylene phosphonic acid); diethylenetriamine penta (methylenephosphonic acid (DTPMP); and mixtures thereof.

4. The composition according to claim 3, wherein said polyphosphonic acid comprises 1-hydroxyethylidene-1,1-diphosphonic acid (HEDP).

5. The composition according to claim 1 wherein the composition has a molar ratio of phosphonate groups to phosphoric acid ($H_3PO_4$) in a range from 1.75:1 to 1.25:1.

6. The composition according to claim 5 wherein the molar ratio of phosphonate groups to phosphoric acid ($H_3PO_4$) is in a range from 1.6:1 to 1.4:1.

7. The composition according to claim 1, wherein said at least one divalent metal cation ($M^{2+}$) is selected from the group consisting of: $Mg^{2+}$; $Ca^{2+}$; $Co^{2+}$; $Ni^{2+}$; $Sr^{2+}$; and $Ba^{2+}$.

8. The composition according to claim 7 comprising $Mg^{2+}$.

9. The composition according to claim 1, wherein the composition has a total concentration of divalent metal cations ($M^{2+}$) in a range from 0.01 to 1 moles/litre.

10. The composition according to claim 9, wherein the total concentration of divalent metal cations ($M^{2+}$) is in a range from 0.01 to 0.5 moles/litre.

11. The composition according to claim 1, wherein in formula (II):
T is selected from Ti, Zr, or Si;
p is 1 or 2;
q is 1;
r is 2, 3, 4, 5 or 6; and,
s is 0, 1, or 2.

12. The composition according to claim 1, wherein said at least one fluoroacid is selected from the group consisting of fluorotitanic acid ($H_2TiF_6$); fluorozirconic acid ($H_2ZrF_6$); fluorosilicic acid ($H_2SiF_6$); fluoroboric acid ($HBF_4$); fluorostannic acid ($H_2SnF_6$);
fluorogermanic acid ($H_2GeF_6$); fluorohafnic acid ($H_2HfF_6$); fluoroaluminic acid ($H_3AlF_6$); and combinations thereof.

13. The composition according to claim 12, wherein said at least one fluoroacid is selected from the group consisting of fluorotitanic acid ($H_2TiF_6$); fluorozirconic acid ($H_2ZrF_6$); and, fluorosilicic acid ($H_2SiF_6$); and combinations thereof.

14. The composition according to claim 1, wherein said at least one fluoroacid is present in an amount such that the composition has a molar ratio of phosphoric acid ($H_3PO_4$) to the element (T) of said fluoroacid in a range from 20:1 to 2:1.

15. The composition according to claim 1 further comprising at least one α-hydroxycarboxylic acid represented by the general formula (III):

$$R_1CH(OH)COOH \tag{III}$$

wherein:
$R_1$ represents a hydrogen atom, a $C_1$-$C_4$ alkyl group, a $C_2$-$C_6$ alkenyl group, a $C_1$-$C_6$ alkoxy group, a $C_3$-$C_6$ cycloalkyl group or a $C_6$-$C_{10}$ aryl group.

16. The composition according to claim 1 being substantially free of peroxide and persulphate compounds.

17. The composition according to claim 1, wherein said at least one fluoroacid is present in an amount such that the composition has a molar ratio of phosphoric acid ($H_3PO_4$) to the element (T) of said fluoroacid in a range from 10:1 to 4:1.

18. A process for imparting a passivate film to a substrate comprising at least one zinc or zinc alloy coated surface, comprising: contacting the at least one zinc or zinc alloy coated surface of the substrate with the aqueous composition of claim 1 at a temperature ranging from 20° C. to 90° C. for a period of time sufficient to form a passivate film thereon.

* * * * *